Sept. 20, 1949. W. J. HAASE Plant Pat. 875
GERANIUM PLANT
Filed July 26, 1948
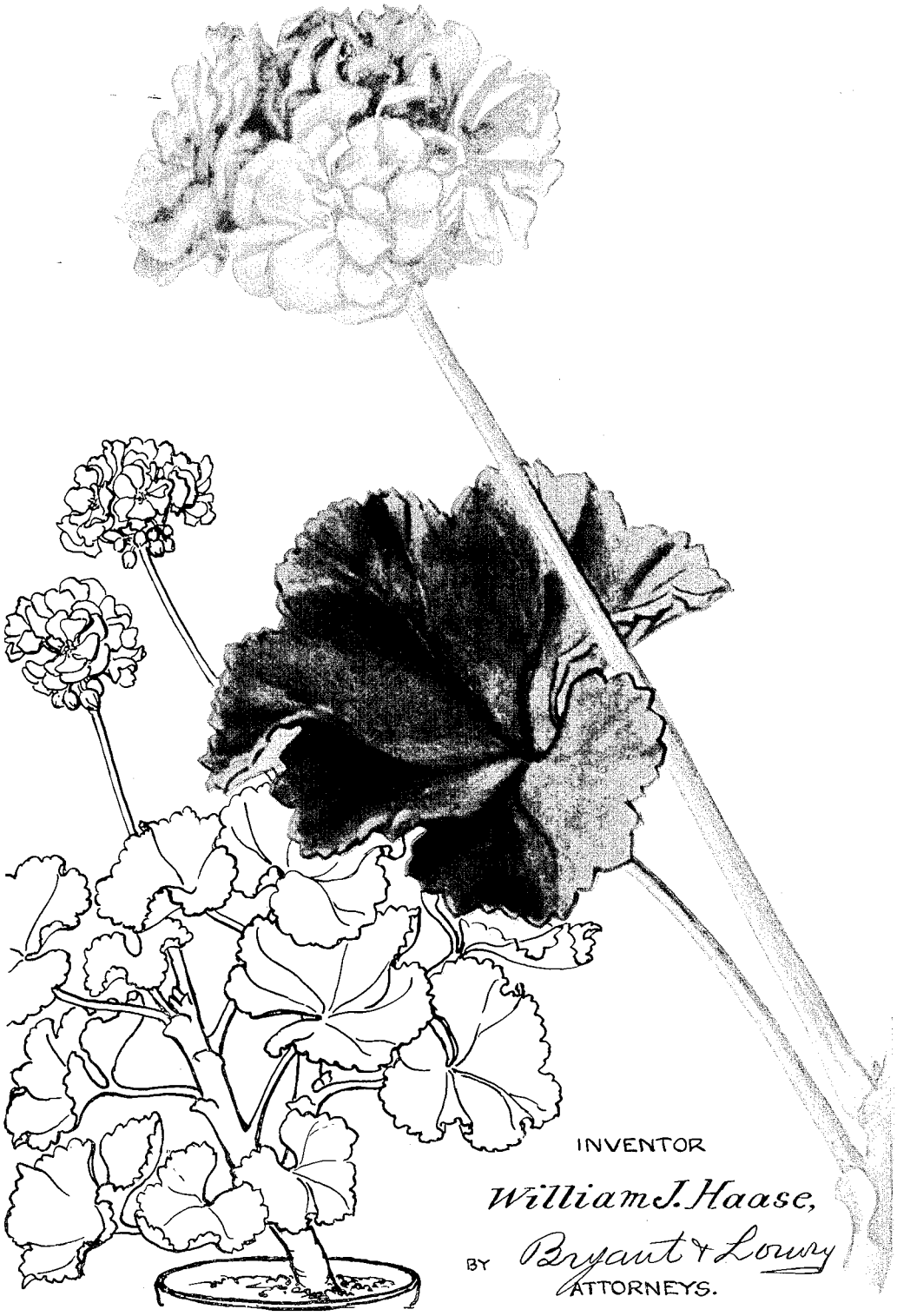

Patented Sept. 20, 1949

Plant Pat. 875

UNITED STATES PATENT OFFICE

875

GERANIUM PLANT

William J. Haase, Peoria, Ill., assignor to Haase Brothers, Peoria, Ill., a partnership Application July 26, 1948, Serial No. 40,775

1 Claim. (Cl. 47—60)

My present discovery relates to an improved variety of geranium plant in the class designed for both commercial pot plant use and for outdoor culture.

It originated as a sport of the variety Radio Red and was discovered by me in our stock beds at Peoria, Illinois Its superior qualities were quickly recognized and vegetative reproduction was soon started. Growth of a number of assexually reproduced plants over several years has proven its qualities to be permanent.

This new variety is excellent for potting or use in windowboxes because of its compact bushy growth, which is also very sturdy, vigorous and healthy. Stems of both flowers and leaves being relatively short and very sturdy and strong, they do not break easily. The foliage is plentiful and presents a vigorous and healthy appearance. It is a little lighter in color than that of many of the older red varieties. A single plant has as many as five or six bloom clusters and as many bud clusters all at one time, on a four-inch pot plant. These are of a perfect scarlet color and provide a very brilliant contrast to the rich green leaves. The color remains brilliant until the flower dies and does not diminish as the season progresses.

Also important commercially is the fact that the variety is a free and continuous bloomer throughout the year and no cultural difficulty is encountered in bringing it into bloom a hundred percent perfectly for Memorial Day (May 30th).

The florets of my new variety are double, the inner row of petals being much smaller than the outer. This is not a common feature among geraniums and is only partially true with its parent which has some single and some double florets, there being no apparent control over the number of each which appears.

The illustrations accompanying these specifications show a leaf and a flower cluster with their respective stems, all in approximately true colors, together with a small black-and-white drawing indicating the type of growth of the plant.

Following is a detailed description of the plant and flower, the color plates referring to Ridgway's Color Standards and Nomenclature.

*The plant*

Growth: Very bushy and compact, with no signs of leggy growth. Grows to a height of 6 to 10 inches. It is a heavy grower because of the large number of breaks from the bottom and sides of the plant. Much heavier and bushier than most other geranium varieties grown under similar conditions. As a producer of cuttings it surpasses any other variety known to me.

Flowering habit: Free and continuous bloomer, having as many as four or five bloom clusters and as many bud clusters at once in the months of April and May. Easily comes into bloom for Decoration Day. Is a heavy producer of bloom both because of the large number of "breaks" and of its tendency to recover quickly after cuttings are taken.

Inflorescence: Umbel or truss formation.

Foliage:

*Color.*—A little lighter than foliage on most of the old varieties. Approximately Forest Green (Plant XVII), usually known as medium green. There is very little indication of a distinct ring in the center of the leaf although the marginal area is slightly darker. The central ring seems more clearly defined under artificial light.

*Appearance.*—Vigorous and healthy.

*Quantity.*—Abundant.

*Size.*—Medium to large. About 3½ to 4 inches across, on a young pot-grown plant, although sometimes larger.

*Texture.*—Heavy. Surface soft and velvety to touch.

*Stems.*—Short and thick. Internodes short. Fuzzy. Approximately Light Bice Green (Plate XVII).

*Peticle or leaf stalk.*—Short and heavy.

*Peduncle or flower stem.*—Extra strong and sturdy. A little longer than leaf stems, but shorter than the usual geranium flower stem.

*The flower*

Truss: Large, usually measuring 4 to 4½ inches across, but often reaching 5 inches. Compact and approximately semi-globular in shape.

Florets:

*Size.*—Diameter 1¼ to 1½ inches.

*Petalage.*—Double, with inner row smaller than outer row.

*Fragrance.*—Mild.

*Color.*—Scarlet (Plate I).

*Petals.*—Smooth-edged, substantial.

*Pedicels.*—Short, approximately 1 inch in length.

*Lasting quality.*—Good.

*Comparison*

The variety known to me which is most like my new variety is its parent, Radio Red. Following are the chief differences between these two varieties:

1. My new variety is a much stronger and bushier grower.

2. My new variety reproduces more prolifically from cuttings.

3. My new variety produces more and larger flower clusters.

4. The color of the flowers of the two varieties differs definitely, that of my new variety being brighter and a more perfect scarlet.

5. The flowers of my variety hold their color much better than those of Radio Red.

6. The florets of my new variety are double, while those of Radio Red are part double and part single with no apparent pattern as to the number of each.

7. The bloom stem of my variety is much stronger.

Having thus disclosed my discovery, I claim:

The new and distinct variety of geranium plant substantially as herein shown and described, characterized particularly by its vigorous, stocky, compact growth, its prolific reproduction from cuttings; its profuse and continuous blooming habit; its abundant foliage of medium green; its short, heavy stems both of flower and of leaf; and its large flower clusters of double-petaled florets of pure scarlet color which continues brilliant throughout the year.

WILLIAM J. HAASE.

No references cited.